United States Patent
Clawson, Jr. et al.

(10) Patent No.: US 9,717,246 B1
(45) Date of Patent: Aug. 1, 2017

(54) METHOD AND RELATED SOLUTION FOR PROTECTING WOOD THROUGH ENHANCED PENETRATION OF WOOD PRESERVATIVES EMPLOYING BUFFERED AMINE OXIDES AND ALKOXYLATED OILS

(71) Applicant: KOP-COAT, INC., Pittsburgh, PA (US)

(72) Inventors: Ronald W. Clawson, Jr., Monroeville, PA (US); Charles N. Cheeks, Oakmont, PA (US)

(73) Assignee: Kop-Coat, Inc., Pittsburgh, PA (US)

( * ) Notice: Subject to any disclaimer, the term of this patent is extended or adjusted under 35 U.S.C. 154(b) by 0 days.

(21) Appl. No.: 15/162,728

(22) Filed: May 24, 2016

(51) Int. Cl.
*A01N 47/12* (2006.01)
*A01N 25/22* (2006.01)
*B27K 3/36* (2006.01)

(52) U.S. Cl.
CPC ............ *A01N 47/12* (2013.01); *A01N 25/22* (2013.01); *B27K 3/36* (2013.01); *B27K 2240/20* (2013.01)

(58) Field of Classification Search
None
See application file for complete search history.

(56) References Cited

U.S. PATENT DOCUMENTS

| | | | |
|---|---|---|---|
| 5,710,103 A | 1/1998 | Magin et al. | |
| 5,833,741 A | 11/1998 | Walker | |
| 5,846,305 A | 12/1998 | Payzant | |
| 6,033,681 A | 3/2000 | Narayanan et al. | |
| 6,274,199 B1 | 8/2001 | Preston et al. | |
| 6,340,384 B1 | 1/2002 | Walker | |
| 6,375,727 B1 | 4/2002 | Walker | |
| 6,416,789 B1 | 7/2002 | Marks et al. | |
| 6,448,279 B1 | 9/2002 | Tseng et al. | |
| 6,508,869 B2 | 1/2003 | Tseng et al. | |
| 6,527,981 B1 | 3/2003 | Tseng et al. | |
| 6,572,788 B2 | 6/2003 | Walker | |
| 6,811,731 B2 | 11/2004 | Archer et al. | |
| 7,056,919 B2 | 6/2006 | Ross et al. | |
| 7,655,281 B2 | 2/2010 | Ward et al. | |
| 7,850,771 B2 | 12/2010 | Cui et al. | |
| 7,896,960 B2 | 3/2011 | Ward et al. | |
| 9,125,398 B2 | 9/2015 | Ross et al. | |
| 9,125,399 B2 | 9/2015 | Ross et al. | |
| 2002/0065206 A1 | 5/2002 | Tseng et al. | |
| 2005/0008576 A1 | 1/2005 | Makansi | |
| 2005/0261130 A1 | 11/2005 | Lennon et al. | |
| 2006/0057300 A1* | 3/2006 | Cui | A01N 25/02 427/440 |
| 2008/0187669 A1* | 8/2008 | Kingma | B27K 3/15 427/342 |
| 2009/0062127 A1 | 3/2009 | Liu | |
| 2009/0088481 A1* | 4/2009 | Ward | A01N 33/12 514/644 |
| 2009/0318294 A1 | 12/2009 | Malec et al. | |
| 2011/0111245 A1 | 5/2011 | Warburton et al. | |
| 2012/0258248 A1 | 10/2012 | Ross et al. | |
| 2013/0172184 A1 | 7/2013 | Bain et al. | |
| 2014/0235445 A1 | 8/2014 | Sanders | |

FOREIGN PATENT DOCUMENTS

| | | |
|---|---|---|
| EP | 1273234 A1 | 1/2002 |
| EP | 2473035 A2 | 7/2012 |
| EP | 2615921 A1 | 7/2013 |
| WO | WO2013189777 A1 | 12/2013 |
| WO | WO2014191096 A1 | 12/2014 |

OTHER PUBLICATIONS

Label for Warrior™ Dandelion and Weed Killer Concentrate.
Label for Roundup® Weed and Grass Killer Concentrate.
Andrew D. Malec, et al., Improving Water Soluble Agricultrual Formulations With Amine Oxides, Proc. ISAA 2013, pp. 85-89.
Mueller et al., Fungicides: Why Fungicides Fail, on pp. 180181 of the Integrated Crop Management, 496 (16) Jun. 19, 2006.
McGrath, M.T 2004. What Are Fungicides. The Plant Health Instructor. DOI: 10.1094/PHII2004082501.
Fishel et al. pH and the Effectiveness of Pesticide, Purdum, E.D. 2002.
Schilder et al. 2012 http://msue.anr.msu.edu/news/How to Get the Most of of Your Fungicide Spray on Fruit Crops.

* cited by examiner

*Primary Examiner* — Robert A Wax
*Assistant Examiner* — Quanglong Truong
(74) *Attorney, Agent, or Firm* — Eckert Seamans Cherin & Mellott, LLC; Arnold B. Silverman

(57) ABSTRACT

The present invention provides improved solutions and related methods for effecting enhanced penetration of wood preservatives through the synergistic action of an amine oxide employed in combination with an alkoxylated oil and a buffering agent. Preferred materials and quantities are recited. The system of the present invention may be employed with artificially stiffened wood.

39 Claims, 1 Drawing Sheet

METHOD AND RELATED SOLUTION FOR PROTECTING WOOD THROUGH ENHANCED PENETRATION OF WOOD PRESERVATIVES EMPLOYING BUFFERED AMINE OXIDES AND ALKOXYLATED OILS

BACKGROUND OF THE INVENTION

1. Field of the Invention

The present invention relates to improved methods and related solutions for effecting enhanced penetration of wood preservatives through the use of buffered amine oxides in combination with alkoxylated oils and also relates to such systems effectively employed with wood which has been stiffened through removal of water therefrom.

2. Description of the Prior Art

It has been known to enhance penetration of wood preservatives into wood through the use of amine oxides combined with buffering agents to achieve a synergistic effect which causes a wood preservative to penetrate the wood to a greater depth. See, for example, U.S. Pat. Nos. 7,655,281; 7,896,960; 9,125,398 and 9,125,399, the disclosures of which are expressly incorporated herein by reference. These patents disclose methods of protecting wood through enhanced penetration of wood preservatives by providing a solution which includes at least one amine oxide, at least one organic wood preservative and a buffering agent. The buffering agent is selected from a group consisting of borate and non-borate based buffering agents. When combined with amine oxides, these enhance the penetration of useful materials into wood.

When wood has been forcefully over dried through kiln conditioning, or unusual ambient climatic conditions, the resulting wood is difficult to penetrate through conventional methods of wood preservation, including mechanical pressure-vacuum impregnation. This overdrying results from water being removed from the wood which causes the wood to become stiffened. There are, in principle, the water may be present in the form of just capillary retention or by loose chemical bonding by hydrogen or by molecular retention. Treating the wood to remove water from one or more of these sources results in the stiffening of the wood. This stiffening of the wood not only improves the structural strength of the wood and enables certain woods so processed to be employed in uses such as building construction wherein, without such stiffening, a specific wood would not have had adequate strength to satisfy building codes and function effectively. The artificially stiffened wood is a result of the pits being closed resisting effective penetration of wood preservative solutions into the woods. The pits can vary in structure related to the specific wood specie, but all are believed to contain a membrane formed from the middle lamella of the cell wall in between adjacent cell walls. These pit membranes are understood to be the major obstacle to efficient penetration of wood preservatives.

The three forms of water contained in wood are: 1. Free water, the bulk of the water contained in the cell lumina is retained only by capillary forces. It is bound chemically and is called "free water". Free water is not the same thermodynamic state as liquid water as energy is required to overcome the capillary forces. Also, free water may contain chemicals thereby altering the drying characteristics of the wood. 2. A second category of water would be bound or hygroscopic water. This is bound to the wood by way of hydrogen bonds. The attraction to wood of free water arises from the presence of the three hydroxal groups (OH) in the hemicellulose and lignin molecules in the cell wall. The hydroxal groups are negatively charged and as water is a polar liquid, the free hydroxal groups in the cellulous are trapped and hold water by hydrogen bonding. 3. Water is also present in the cell lumina in the form of water vapor, but this is normally negligible at normal temperature and geminity.

There remains, however, a need for improved methods and solutions for effectively delivering wood preservatives to an enhanced depth even with respect to hard to penetrate woods such as forcibly overdried woods.

SUMMARY OF THE INVENTION

The hereinbefore described need has been met by the wood preservation solution and associated method of the present invention. The solution contains an amine oxide, a wood preservative, an alkoxylated oil and a buffering agent, which combine to establish a synergistic effect to produce greater depth of penetration of the wood preservative into the wood. The results from the extensive testing of the amine oxide in combination with ethoxylated castor oil, tall oil or soya oil and a wood preservative are presented in TABLES 1 through 9 of the present invention with propoxylated castor oil having been tested and reported in TABLE 10. The buffering agent is preferably a dual buffering agent.

It has been discovered that the inclusion of alkoxylated oils in buffered amine oxide treating solutions enhance the penetration of useful materials into wood including difficult to treat wood such as artificially stiffened wood. In the case of over dried wood, the penetration has been shown to be complete when applied to the wood using a non-mechanical assisted impregnation, such as a dip.

It is an object of present invention to provide a method and related solution for enhancing penetration of wood preservatives in wood including wood which has been forcefully overdried in order to establish artificially stiffened wood.

It is a further object of the present invention to provide such a method and solution which does not require the use of pressure in order to enhance penetration of wood preservatives.

It is another object of the present invention to employ alkoxylated oils or in combination with buffered amine oxide to effect the desired penetration.

It is yet another object of the present invention to enhance the performance of the systems disclosed in U.S. Pat. Nos. 7,655,281; 7,896,960; 9,125,398 and 9,125,399.

It is yet another object of the present invention to effect enhanced depth penetration of both hardwoods and softwoods, regardless of whether they have been forcefully overdried to create artificially stiffened wood.

It is yet another object of the present invention to provide such a method and solution which is compatible with existing systems for delivering wood preservatives to the desired depth of penetration.

These and other objects of the invention will be more fully understood from the following description of the invention on reference to the illustration appended hereto.

DESCRIPTION OF THE PREFERRED EMBODIMENTS

Figure 1:
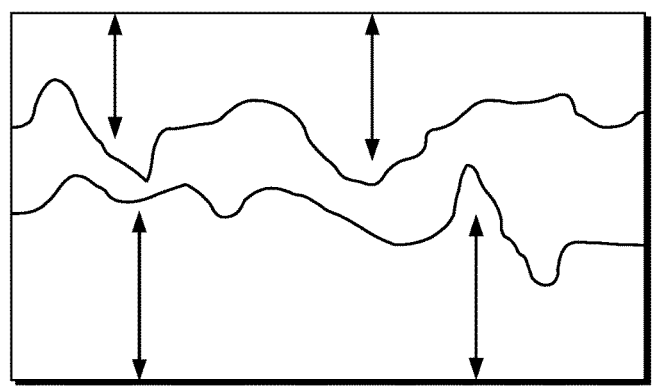
FIG. 1 is a schematic illustration of a cross-section of a portion of a wood sample illustrative of the measurement of depth of penetration of wood preservatives.

As employed herein, the terms "buffering agent" or "buffered" is an aqueous solution consisting of a mixture of a weak acid and its conjugate base or a weak base and its conjugate acid. It has the property that the pH of the solution changes very little when a small amount of a strong acid or strong base is added to it. Buffered solutions are used as a means of keeping pH at a nearly constant value in a wide range of chemical operations. In the present system, the buffer helps to maintain a neutral to basic pH in the presence of the acids naturally present in the wood. As the pH of wood is typically around 5.4, the preferred buffering capacity should be above a pH of 5.4 in order to achieve maximum penetration. These terms will include, but not be limited to, boric acid, borax, disodium octaborate, phosphates, calcium phosphates, calcium hydroxide, as well as other effective buffering materials and combinations thereof. A dual buffering system consists of two different buffering agents, each with their own weak acid/conjugate base or weak base/conjugate acid pairs, which combine to provide the desired pH.

As employed herein, "wood" means wood, wood-based materials, wood fiber materials, forest products, timber, lumber, engineered wood, millwork, joinery, wood laminates, laminated veneer lumber, plywood, laminated strand lumber, wood fiber composites, medium density fiberboard, particle board, hard board, oriented strand board, wood fiber resin composites, wood strand resin composites, wood particle resin composites and other wood and wood fiber-based materials and fabricated and semi-fabricated items made therefrom.

As employed herein, "artificially stiffened" wood means wood which has achieved enhanced stiffness through kiln treatment so as to force dry the wood in a manner that removal of at least a substantial portion of water entrapped within the tree and molecular water is achieved. This includes (a) entrapped water held within the tree by capillary forces generally referred to as "free water", (b) hygroscopic water, and (c) molecular water removed from the polymeric structures of the wood fiber.

As employed herein, the term "wood preservatives" means organic compounds, halo-organic compounds, metalo-organic compounds, organo-salts, borates, organo-phosphates and non-organoboron compounds having fungicidal, insecticidal, water-resistant, termite-resisting, decay-resisting, stain-resisting or other wood-protective properties.

As used herein, the term "amine oxide" or "amine oxide compound" refers to those compounds which are formed as reaction products in the reaction of tertiary amines and hydrogen peroxides and are represented by the general formula:

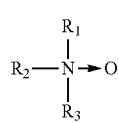

(1)

where $R_1$, $R_2$ and $R_3$ are independent and can be a linear, branched, cyclic, aromatic or any combination thereof of saturated or unsaturated C1 to C20 group and any C2-C20 carbon atom can be replaced with a hetero-atom selected from the group consisting of O, S and N.

Preferred amine oxides are alkyl dimethyl amine oxides such as decyl dimethyl amine oxide, lauryl dimethyl amine oxide, isoalkyl dimethyl amine oxide, myristyl dimethyl amine oxide, cetyl dimethyl amine oxide, stearyl dimethyl amine oxide and octyl dimethyl amine oxide. Most preferred is N-alkyl (C12-C16)-N,N-dimethyl AO.

As used herein, the term "buffered amine oxide" means amine oxide which has been buffered employing a buffering agent, As used herein, the term "alkoxylated oil" means an aliphatic or aromatic chain oil in which the hydroxyl groups have been reacted with ethylene oxide to form polyethylene glycol ethers. The parent oil can be of petrochemical or of plant based origin. When extracted from plants, the materials are commonly referred to as vegetable oils. Vegetable oils are classified as trigylcerides, which is an ester derived from glycerol and three fatty acids, that have been extracted from living and/or harvested plants. These triglycerides can be of the unsaturated or saturated types. Unsaturated triglycerides contain double and/or triple bonds in their skeletal carbon chains, while saturated variants contain only single bonds. Like most economically important hydrocarbon based raw materials extracted from plants or petrochemical based sources, the oils that are reacted with ethylene oxide to form the alkoxylated oils, contain fractions of multiple carbon chain lengths. For example, ethoxylated castor oil, which is produced through the reaction of castor oil and ethylene oxide contains primarily carbon chains of 18, with small amounts of 16, 14 and 12 chain length compounds. Propoxylated fatty acid is produced by reacting an oil with propylene oxide. The most common alkoxylated oils utilized within various industries are those made from parent castor oil, tall oil, and soybean oil. Alkoxylated oils are specified based on percentage of ethylene oxide (% EO). These values are averages across all of the castor oil chains in solution. The % EO reported can have minimums of +30% EO.

EXAMPLES

Tests were performed to evaluate the effectiveness of the solution and methods of the present invention.

Various aqueous buffered amine oxide systems were prepared by dissolving the appropriate reagents into deionized water. Key pesticide based wood preservatives and benign process chemicals were added into the buffered amine oxides. Alkoxylated oils were then added and the solution was stirred until homogeneous.

All treatment solutions were based on a 1000 gram total batch size. To the appropriate amount of distilled water was added the individual dual buffer pairs. While, being continuously stirred, the solution was heated to 60° C. before adding the amine oxide source. The process chemicals Dipropylene Glycol Monoethyl ether and PEG 400 were added and the solution was allowed to stir for 5 minutes. Next, 3-Iodoprop-2-yn-1-yl butylcarbamate (and/or any other preservative) was added and stirred until fully dissolved. The ethoxylated oil was then added and the solution stirred until homogeneous.

Among the preferred oils are castor oil which can be reactive with ethylene oxide in order to convert the castor oil which in insoluble in water into a water emulsifiable castor oil. The preferred alkoxylated oils are selected from the group consisting of ethoxylated castor, ethoxylated tall oil, ethoxylated soya oil and propoxylated castor oil.

The tests were performed on artificially stiffened wood. It has been found that the stiffening of certain wood in order to create artificially stiffened wood enhances the physical properties and make them usable for such things as framing, can be made practical through the present invention as the invention's ability to enhance penetration. Among the woods within be benefited most through artificial stiffening are spruce, pine and fir although other woods having similar strength characteristics can have the stiffness properties enhanced to provide properties which are more suitable for certain uses as in building construction for example.

Canadian sourced SPF (Spruce-Pine-Fir) boards (12 in by 3.5 in by 1.5 in) were treated with each treatment solution by dipping it into the hot (60-65° C.) solution for 5 minutes. All samples were matched by being cut from the same 20 foot parent boards. Boards were then wrapped under plastic for a 96 hour activation period.

After the activation period, one-inch thick cross sections were cut four inches from the sealed end of each board for measurement of penetration of active ingredients. Each cross-section was then heated in an oven at 175° C. for 10 minutes. After removal from the oven, a bromophenol blue indicator solution (0.4%) or an alcoholic Circumin indicator solution was applied to each cross sectional face.

The bromophenol blue indicator changes color from light green to dark blue in the presence of the amine oxides present in the treating solution. As a result, the degree of penetration of the amine oxides can be monitored by noting the depth of the dark blue color present in each cross-sectional face.

The Circumin indicator changes from a pale yellow to a bright red solution in the presence of boron. The color change is boron concentration dependent, so the acceptable colors may vary from the bright red, to orange, to a pale pink. To ensure a positive colorimetric result is acknowledged in the treated samples, an untreated control piece of the same species of wood with the indicators applied was provided.

After the bromophenol blue or Circumin indicator had been present on the face of each cross-sectional sample for five minutes, a marker was used to trace the depth of penetration of the amine oxide or boron toward the center of each sample. This distance is indicated by the double arrows shown in FIG. 1.

In FIG. 1, the double headed arrows indicating the depth of penetration of the wood preservative from either the upper wood surface or the lower wood surface.

Figure 2:
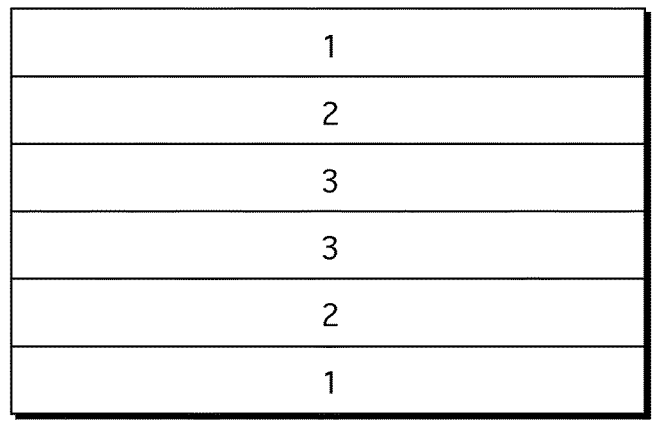
FIG. 2 is a schematic illustration of the scoring zones for measuring depth of penetration of the samples.

With reference to FIG. 2, to accurately measure the depth of penetration, the cross-section of the samples were conveniently divided into equal sections. Penetration was scored as 1, 2, or 3 from each side and then averaged together. The penetration score for each treatment was an average of 7 samples.

Figure 3:
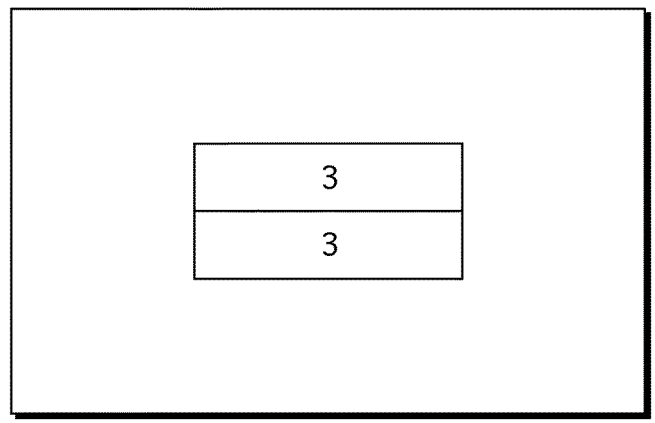
FIG. 3 is a cross-sectional view showing schematically showing the central zones.

Referring to FIG. 3, to analytically verify the proof of the preservatives in the deepest zones, a geometrical central 9th sample was extracted and subjected to analytical testing. This consisted of the geometrical centers of both 3 zones.

Analysis was conducted using wood preservation-industry standard Neutron Activation Analysis (NAA). This non-destructive analysis involves the bombardment of the samples with energy used to excite specific elements found within the pesticide molecules. Specialized detectors are used to quantitatively verify the presence of these molecules in these zones. Untreated species-specific wood samples are included to validate the analyses.

The following tables summarize the testing used to determine and establish the enhanced penetration seen when utilizing the combination of ethoxylated oils, amine oxides, and buffers.

Table 1 represents solutions A-G comparing the penetration of various solutions when evaluating the inclusion of amine oxides, buffers, and ethoxylated castor oil.

Table 2 represents solutions H-N comparing low amine oxides (H) and low buffers (I) when amine oxides and ethoxylated castor oils are held constant. Solutions J-N represent non-borate, or alternate buffer systems when used the baseline amounts of ethoxylated castor oil, amine oxides, and buffers.

Table 3 represents data collected with solutions (O-Q) with varying amounts of ethoxylated castor oil when the amine oxides and buffers are held constant.

Tables 4 and 5 represent solutions (R and S) containing Ethoxylated Tall Oil and Ethoxylated Soybean Oil, respectively, in place of ethoxylated Castor oil to show that other alkoxylated oils can be utilized to demonstrate the same improved penetration.

Table 6 contains the data for a buffered amine oxide/ethoxylated castor oil containing solution (T) that contains triazole, and a synthetic pyrtheroid to demonstrate that the technology extends to various biocides.

Table 7 represents a buffered amine oxide/ethoxylated castor oil solution (U) that contains an inorganic copper complex that is paired with an organic quaternary ammonium compound.

Table 8 represents data from a solution (V) containing amine oxides, buffers, and ethoxylated castor oil where the amine oxide is a shorter chain length to demonstrate that carbon chains of multiple lengths produce the same enhanced penetration.

Table 9 represents the preferred treating solution used on easy to treat species such as Radiata Pine and Yellow Poplar. This was the solution of a test (TABLE 1) used previously on SPF (Spruce-Pine-Fir) in the test shown in TABLES 1-8 and 10.

Table 10 represents a solution containing an alternate fatty acid with the amine oxides and buffers. In this solution W, a propoxylated castor oil was utilized. This material is produced by the reaction of propylene oxide and castor oil.

In all of the following examples, if the score of penetration was 2.1 or greater, this was deemed to provide effective, enhanced penetration. If the score was less than 2.0, this was not deemed adequate. The reference to "yes" and "no" at the bottom of the columns reflects the application of this standard.

The amine oxide employed in all of the tests was Delta 4000 which had carbon lengths in the range of about C12 to C16.

Castor oils are insoluble in water. By reacting ethylene oxide with castor oil, a water emulsifiable ethoxylated castor oil is created.

All of the tests reported in TABLES 1 through 10 employed water as the solvent to create the test solution. If desired, the solution can be created as a concentrate with additional water being added later to create the solution ready for use.

TABLE 1

|  | A | | B | | C | | D | | E | | F | | G | |
|---|---|---|---|---|---|---|---|---|---|---|---|---|---|---|
|  | % (m/m) | mol | % (m/m) | mol | % (m/m) | mol | % (m/m) | mol | % (m/m) | mol | % (m/m) | mol | % (m/m) | mol |
| Delta 4000 (60% ai C12-16 N-alkyl N,N-dimethyl AO) | 5 | 0.013 | 5 | 0.013 |  |  | 5 | 0.013 |  |  | 5 | 0.0218 |  |  |
| Ethoxylated Castor Oil (2900 amu, 68% EO) | 4 | 0.001 |  | 0 | 4 | 0.001 | 4 | 0.001 | 4 | 0.001 |  |  |  |  |
| IPBC | 0.51 | 0.002 | 0.51 | 0.002 | 0.51 | 0.002 | 0.51 | 0.002 | 0.51 | 0.002 | 0.51 | 0.00181 | 0.51 | 0.002 |
| PEG 400 | 4.6 | 0.012 | 4.6 | 0.012 | 4.6 | 0.012 | 4.6 | 0.012 | 4.6 | 0.012 | 4.6 | 0.0115 | 4.6 | 0.012 |
| Dipropylene Glycol Monoethyl ether | 2 | 0.013 | 2 | 0.013 | 2 | 0.013 | 2 | 0.013 | 2 | 0.013 | 2 | 0.013 | 2 | 0.013 |
| Water | 62.26 | 3.459 | 66.26 | 3.681 | 67.26 | 3.737 | 83.89 | 4.661 | 88.89 | 4.938 | 87.89 | 4.88278 | 71.26 | 3.959 |
| Buffer System |  |  |  |  |  |  |  |  |  |  |  |  |  |  |
| 1  Borax | 10.89 | 0.037 | 10.89 | 0.037 | 10.89 | 0.037 |  |  |  |  |  |  | 10.89 | 0.037 |
|      Boric Acid | 10.74 | 0.174 | 10.74 | 0.174 | 10.74 | 0.174 |  |  |  |  |  |  | 10.74 | 0.174 |
| 2  Sodium Carbonate |  |  |  |  |  |  |  |  |  |  |  |  |  |  |
|      Sodium Bicarbonate |  |  |  |  |  |  |  |  |  |  |  |  |  |  |
| 3  Potassium Carbonate |  |  |  |  |  |  |  |  |  |  |  |  |  |  |
|      Potassium Bicarbonate |  |  |  |  |  |  |  |  |  |  |  |  |  |  |
| 4  Ammonium Chloride |  |  |  |  |  |  |  |  |  |  |  |  |  |  |
|      Sodium Hydroxide |  |  |  |  |  |  |  |  |  |  |  |  |  |  |
| 5  Ammonium Citrate Tribasic |  |  |  |  |  |  |  |  |  |  |  |  |  |  |
| 6  Monopotassium phosphate |  |  |  |  |  |  |  |  |  |  |  |  |  |  |
|      Dipotassium phosphate |  |  |  |  |  |  |  |  |  |  |  |  |  |  |
| pH of treating solution | 7.5 |  | 7.5 |  | 7.5 |  | 8.1 |  | 8.1 |  | 8.1 |  | 7.5 |  |
| Penetration Zone (average of 10 samples) | 3.0 |  | 2.1 |  | 1.3 |  | 1.3 |  | 1.4 |  | 1.4 |  | 0.7 |  |
| Analytical Proof of Penetration (NAA via I-) | Yes |  | Yes |  | No |  | No |  | No |  | No |  | No |  |
| Total | 100 |  | 100 |  | 100 |  | 100 |  | 100 |  | 100 |  | 100 |  |
| Total Non-Water Components | 37.74 |  | 33.74 |  | 32.74 |  | 16.11 |  | 11.11 |  | 12.11 |  | 28.74 |  |

Referring to TABLE 1, in test A, 5% (m/m) (mass to mass of component to total solution mass) amine oxide was employed with 4% ethoxylated castor oil having a mass of 2900 and having 68% ethoxylated oil. Fungicide IPBC (iodopropynyl butylcarbamate) was employed with solvents PEG 400 and Dipropylene Glycol Monoethyl ether with 62.26% water. The pH of this solution was 7.5 and penetration point average of 10 samples was 3.0 which is 100% penetration. The buffer system was a combination of borax and boric acid in the quantities shown.

In test B, the 5% (m/m) amine oxide was employed, but no ethoxylated castor oil was used. The identical quantity of buffer was employed. This yielded 2.1 penetration. Both tests, A and B illustrate an effective depth of penetration. The comparative data shows that the presence of the ethoxylated castor oil in Test A provided a superior result to Test B which was substantially identical to Test A except for Test B not having the ethoxylated castor oil.

Test C, showed no amine oxide being use with 4% ethoxylated castor oil being used and the identical amount of buffer as previously used. This produced an unsuccessful penetration of 1.3.

Tests D, E and F show, respectively, the use of amine oxide and ethoxylated castor oil (D), the use of ethoxylated castor oil without amine oxide, and the use of amine oxide without castor oil, but no buffer being employed. In each of cases (C-F), the depth of penetration had an unsuccessful score in the range of 1.3 to 1.4.

Finally, in test G, neither amine oxide nor ethoxylated castor oil was employed with the identical quantities of the buffer system being employed with the result being 0.7 which was inadequate penetration.

TABLE 1, therefore, shows that maximum benefit is obtained through the parameters used in Test A and lesser, but nevertheless successful, depth penetration was obtained in Test B.

TABLE 2

|  | H | | I | | J | | K | | L | | M | | N | |
|---|---|---|---|---|---|---|---|---|---|---|---|---|---|---|
|  | % (m/m) | mol | % (m/m) | mol | % (m/m) | mol | % (m/m) | mol | % (m/m) | mol | % (m/m) | mol | % (m/m) | mol |
| Delta 4000 (60% ai C12-16 N-alkyl N,N-dimethyl AO) | 0.16 | 4E-04 | 0.16 | 4E-04 | 5 | 0.022 | 5 | 0.013 | 5 | 0.022 | 5 | 0.0218 | 5 | 0.022 |
| Ethoxylated Castor Oil (2900 amu, 68% EO) | 4 | 0.001 | 4 | 0.001 | 4 | 0.001 | 4 | 0.001 | 4 | 0.001 | 4 | 0.00138 | 4 | 0.001 |
| IPBC | 0.51 | 0.002 | 0.51 | 0.002 | 0.51 | 0.002 | 0.51 | 0.002 | 0.51 | 0.002 | 0.51 | 0.00181 | 0.51 | 0.002 |
| PEG 400 | 4.6 | 0.012 | 4.6 | 0.012 | 4.6 | 0.012 | 4.6 | 0.012 | 4.6 | 0.012 | 4.6 | 0.0115 | 4.6 | 0.012 |
| Dipropylene Glycol Monoethyl ether | 2 | 0.013 | 2 | 0.013 | 2 | 0.013 | 2 | 0.013 | 2 | 0.013 | 2 | 0.0135 | 2 | 0.013 |

TABLE 2-continued

| | H | | I | | J | | K | | L | | M | | N | |
|---|---|---|---|---|---|---|---|---|---|---|---|---|---|---|
| | % (m/m) | mol | % (m/m) | mol | % (m/m) | mol | % (m/m) | mol | % (m/m) | mol | % (m/m) | mol | % (m/m) | mol |
| Water | 67.1 | 3.728 | 83.73 | 4.652 | 79.15 | 4.397 | 77.98 | 4.332 | 80.22 | 4.457 | 71.73 | 3.985 | 76.13 | 4.229 |
| Buffer System | | | | | | | | | | | | | | |
| 1  Borax | 10.89 | 0.037 | 2.31 | 0.008 | | | | | | | | | | |
|     Boric Acid | 10.74 | 0.174 | 2.69 | 0.0044 | | | | | | | | | | |
| 2  Sodium Carbonate | | | | | 2.64 | 0.025 | | | | | | | | |
|     Sodium Bicarbonate | | | | | 2.1 | 0.025 | | | | | | | | |
| 3  Potassium Carbonate | | | | | | | 3.45 | 0.025 | | | | | | |
|     Potassium Bicarbonate | | | | | | | 2.46 | 0.025 | | | | | | |
| 4  Ammonium Chloride | | | | | | | | | 2.67 | 0.05 | | | | |
|     Sodium Hydroxide | | | | | | | | | 1 | 0.025 | | | | |
| 5  Ammonium Citrate Tribasic | | | | | | | | | | | 12.16 | 0.05 | | |
| 6  Monopotassium phosphate | | | | | | | | | | | | | 3.4 | 0.025 |
|     Dipotassium phosphate | | | | | | | | | | | | | 4.36 | 0.025 |
| pH of treating solution | 7.5 | | 7.5 | | 9.8 | | 10 | | 10.4 | | 7.5 | | 7.4 | |
| Penetration Zone (average of 10 samples) | 2.3 | | 2.1 | | 2.6 | | 2.6 | | 2.1 | | 2.1 | | 2.1 | |
| Analytical Proof of Penetration (NAA via I-) | Yes | | Yes | | Yes | | Yes | | Yes | | Yes | | Yes | |
| Total | 100 | | 100 | | 100 | | 100 | | 100 | | 100 | | 100 | |
| Total Non-Water Components | 32.9 | | 16.27 | | 20.85 | | 22.02 | | 19.78 | | 28.27 | | 23.87 | |

TABLE 2 shows the use of the same basic ingredients as in TABLE 1, except different buffer systems were employed in certain tests.

In TABLE 2, in test H, the amine oxide was reduced to 0.16% (m/m) with remaining constituents being essentially the same as Test A, except that additional dual buffers 2 through 6 were tested. The reduction in amine oxide resulted in acceptable penetration, but to a depth of 2.3 as contrasted with 3.0 in Test A. Considering Test I, the amine oxide fungicide and solvents remain the same as in Test H, but the buffer system amounts were reduced substantially. This produced a successful penetration of 2.1, but one which was less than that in Test H.

Tests J through N all produce successful penetrations in the ranges of 2.1 to 3.6 employing different buffer systems. These buffer systems are identified by the numbers 2 through 6 were dual buffer systems.

In Tests J through L, the amount of buffer employed was substantially lower than that in Test H and yet the penetration was equal to or higher. In summary, each of the tests shown in TABLE 2 resulted in a successful death of penetration.

TABLE 3

| | O | | P | | Q | |
|---|---|---|---|---|---|---|
| | % (m/m) | mol | % (m/m) | mol | % (m/m) | mol |
| Delta 4000 (60% ai C12-16 N-alkyl N,N-dimethyl AO) | 5 | 0.013 | 5 | 0.013 | 5 | 0.013 |
| Ethoxylated Castor Oil (2900 amu, 68% EO) | 0.5 | 2E−04 | 2 | 7E−04 | 6 | 0.002 |
| IPBC | 0.51 | 0.002 | 0.51 | 0.002 | 0.51 | 0.002 |
| PEG 400 | 4.6 | 0.012 | 4.6 | 0.012 | 4.6 | 0.012 |
| Dipropylene Glycol Monoethyl ether | 2 | 0.013 | 2 | 0.013 | 2 | 0.013 |
| Water | 65.76 | 3.653 | 64.26 | 3.57 | 60.26 | 3.348 |
| Buffer System | | | | | | |
| 1  Borax | 10.89 | 0.037 | 10.89 | 0.037 | 10.89 | 0.037 |
|     Boric Acid | 10.74 | 0.174 | 10.74 | 0.174 | 10.74 | 0.174 |
| 2  Sodium Carbonate | | | | | | |
|     Sodium Bicarbonate | | | | | | |
| 3  Potassium Carbonate | | | | | | |
|     Potassium Bicarbonate | | | | | | |
| 4  Ammonium Chloride | | | | | | |
|     Sodium Hydroxide | | | | | | |
| 5  Ammonium Citrate Tribasic | | | | | | |
| 6  Monopotassium phosphate | | | | | | |
|     Dipotassium phosphate | | | | | | |
| pH of treating solution | 7.5 | | 7.5 | | 7.6 | |

TABLE 3-continued

| | O | | P | | Q | |
|---|---|---|---|---|---|---|
| | % (m/m) | mol | % (m/m) | mol | % (m/m) | mol |
| Penetration Zone (average of 10 samples) | 2.6 | | 2.4 | | 3.0 | |
| Analytical Proof of Penetration (NAA via I-) | Yes | | Yes | | Yes | |
| Total | 100 | | 100 | | 100 | |
| Total Non-Water Components | 34.24 | | 35.74 | | 39.74 | |

Turning to TABLE 3, these tests showed the use of 5% (m/m) of the amine oxide. Test O showed only 0.5% ethoxylated castor oil, but had a yield of a depth of 2.6. A reduction of the ethoxylated castor oil to 2% (m/m) in Test P resulted in successful depth of penetration. Test Q, which increased ethoxylated castor oil to 6% (m/m), achieved the maximum score of 3.0.

Among the preferred ethoxylated derivatives are ethoxylated tall oil (TABLE 4), ethoxylated soya oil (TABLE 5) and groundnut oils.

TABLE 4

| | R | |
|---|---|---|
| | % (m/m) | mol |
| Delta 4000 (60% ai C12-16 N-alkyl N,N-dimethyl AO) | 5 | 0.013 |
| Ethoxylated Tall Oil (2009 amu, 52% EO) | 4 | 0.002 |
| IPBC | 0.51 | 0.002 |
| PEG 400 | 4.6 | 0.012 |
| Dipropylene Glycol Monoethyl ether | 2 | 0.013 |
| Water | 62.26 | 3.459 |
| Buffer System | | |
| 1    Borax | 10.89 | 0.037 |
|      Boric Acid | 10.74 | 0.174 |
| 2    Sodium Carbonate | | |
|      Sodium Bicarbonate | | |
| 3    Potassium Carbonate | | |
|      Potassium Bicarbonate | | |
| 4    Ammonium Chloride | | |
|      Sodium Hydroxide | | |
| 5    Ammonium Citrate Tribasic | | |
| 6    Monopotassium phosphate | | |
|      Dipotassium phosphate | | |
|      pH of treating solution | 7.5 | |
| Penetration Zone (average of 10 samples) | 2.9 | |
| Analytical Proof of Penetration (NAA via I-) | Yes | |
| Total | 100 | |
| Total Non-Water Components | 37.74 | |

TABLE 4 shows the use of ethoxylated tall oil in combination with amine oxide and the borax/boric acid buffer system. With the other constituents remaining essentially the same, a high penetration of 2.9 was achieved.

TABLE 5

| | S | |
|---|---|---|
| | % (m/m) | mol |
| Delta 4000 (60% ai C12-16 N-alkyl N,N-dimethyl AO) | 5 | 0.013 |
| Ethoxylated Soya Oil (1500 amu, 61% EO) | 4 | 0.003 |
| IPBC | 0.51 | 0.002 |
| PEG 400 | 4.6 | 0.012 |
| Dipropylene Glycol Monoethyl ether | 2 | 0.013 |
| Water | 62.26 | 3.459 |
| Buffer System | | |
| 1    Borax | 10.89 | 0.037 |
|      Boric Acid | 10.74 | 0.174 |
| 2    Sodium Carbonate | | |
|      Sodium Bicarbonate | | |
| 3    Potassium Carbonate | | |
|      Potassium Bicarbonate | | |
| 4    Ammonium Chloride | | |
|      Sodium Hydroxide | | |
| 5    Ammonium Citrate Tribasic | | |
| 6    Monopotassium phosphate | | |
|      Dipotassium phosphate | | |
|      pH of treating solution | 7.5 | |
| Penetration Zone (average of 10 samples) | 2.9 | |
| Analytical Proof of Penetration (NAA via I-) | Yes | |
| Total | 100 | |
| Total Non-Water Components | 37.74 | |

TABLE 5 shows the results of the use of ethoxylated soya oil having a mass of 1500 and 61% EO. The use of ethoxylated soya oil in the amount of 4% with the other constituents remaining essentially the same resulted in a successful penetration of 2.9.

TABLE 6

| | T | |
|---|---|---|
| | % (m/m) | mol |
| Delta 4000 (60% ai C12-16 N-alkyl N,N-dimethyl AO) | 5 | 0.013 |
| Ethoxylated Castor Oil (2900 amu, 68% EO) | 4 | 0.001 |
| IPBC | 0.51 | 0.002 |
| Propiconazole | 0.21 | 6E-04 |
| Tebuconazole | 0.21 | 7E-04 |
| Permethrin | 5 | 0.001 |
| PEG 400 | 4.6 | 0.012 |
| Dipropylene Glycol Monoethyl ether | 2 | 0.013 |
| Water | 62.26 | 3.408 |
| Buffer System | | |
| 1    Borax | 10.89 | 0.037 |
|      Boric Acid | 10.74 | 0.174 |
| 2    Sodium Carbonate | | |
|      Sodium Bicarbonate | | |
| 3    Potassium Carbonate | | |
|      Potassium Bicarbonate | | |
| 4    Ammonium Chloride | | |
|      Sodium Hydroxide | | |
| 5    Ammonium Citrate Tribasic | | |

TABLE 6-continued

| | | T | |
|---|---|---|---|
| | | % (m/m) | mol |
| 6 | Monopotassium phosphate | | |
| | Dipotassium phosphate | | |
| | pH of treating solution | 7.5 | |
| Penetration Zone (average of 10 samples) | | 2.9 | |
| Analytical Proof of Penetration (NAA via I-) | | Yes | |
| Total | | 100 | |
| Total Non-Water Components | | 38.66 | |

TABLE 6 shows the result of the use of two fungicides (Propiconazole, Tebuconazole), and Permethrin, an insecticide, in combination with amine oxide, ethoxylated castor oil and a buffer. The results showed a successful penetration of 2.9.

TABLE 7

| | U | |
|---|---|---|
| | % (m/m) | mol |
| Delta 4000 (60% ai C12-16 N-alkyl N,N-dimethyl AO) | 5 | 0.013 |
| Ethoxylated Castor Oil (2900 amu, 68% EO) | 4 | 0.001 |
| Alkaline Copper Quat | 3 | 0.014 |
| DDACarb | 1.7 | 0.004 |
| PEG 400 | 4.6 | 0.012 |
| Dipropylene Glycol Monoethyl ether | 2 | 0.013 |
| Water | 58.103 | 3.228 |
| Buffer System | | |
| 1  Borax | 10.89 | 0.037 |
| Boric Acid | 10.74 | 0.174 |
| 2  Sodium Carbonate | | |
| Sodium Bicarbonate | | |
| 3  Potassium Carbonate | | |
| Potassium Bicarbonate | | |
| 4  Ammonium Chloride | | |
| Sodium Hydroxide | | |
| 5  Ammonium Citrate Tribasic | | |
| 6  Monopotassium phosphate | | |
| Dipotassium phosphate | | |
| pH of treating solution | 9.2 | |
| Penetration Zone (average of 10 samples) | 2.3 | |
| Analytical Proof of Penetration (NAA via I-) | Yes | |
| Total | 100 | |
| Total Non-Water Components | 41.897 | |

With regard to TABLE 7, an alkaline copper quaternary ammonium compound was employed in the amount of 3% and DDACarb in the amount of 1.7% was employed along with the borax/boric acid buffer system. This produced a successful 2.3 penetration.

The tests reported in TABLE 7 employed an inorganic copper based preservative as contrasted with other preservatives tested which were organic preservatives.

TABLE 8

| | V | |
|---|---|---|
| | % (m/m) | mol |
| Decyl Dimethyl Amine Oxide (C10) | 5 | 0.015 |
| Ethoxylated Castor Oil (2900 amu, 68% EO) | 4 | 0.001 |

TABLE 8-continued

| | V | |
|---|---|---|
| | % (m/m) | mol |
| IPBC | 0.51 | 0.002 |
| PEG 400 | 4.6 | 0.012 |
| Dipropylene Glycol Monoethyl ether | 2 | 0.013 |
| Water | 62.26 | 3.459 |
| Buffer System | | |
| 1  Borax | 10.89 | 0.037 |
| Boric Acid | 10.74 | 0.174 |
| 2  Sodium Carbonate | | |
| Sodium Bicarbonate | | |
| 3  Potassium Carbonate | | |
| Potassium Bicarbonate | | |
| 4  Ammonium Chloride | | |
| Sodium Hydroxide | | |
| 5  Ammonium Citrate Tribasic | | |
| 6  Monopotassium phosphate | | |
| Dipotassium phosphate | | |
| pH of treating solution | 7.5 | |
| Penetration Zone (average of 10 samples) | 3.0 | |
| Analytical Proof of Penetration (NAA via I-) | Yes | |
| Total | 100 | |
| Total Non-Water Components | 37.74 | |

Referring to TABLE 8, it is noted that the amine oxide has a carbon chain length 10 as contrasted with the prior tables wherein the length was C12 to C16. The fungicide IPBC was employed along with borax/boric acid buffer. This showed the 5% amine oxide m/m and 4% ethoxylated castor oil 2900 amu provided a maximum penetration of 3.0.

TABLE 9

| | Radiata Pine | | Yellow Poplar | |
|---|---|---|---|---|
| | % (m/m) | mol | % (m/m) | mol |
| Delta 4000 (60% ai C12-16 N-alkyl N,N-dimethyl AO) | 5 | 0.013 | 5 | 0.013 |
| Ethoxylated Castor Oil (2900 amu, 68% EO) | 4 | 0.001 | 4 | 0.001 |
| IPBC | 0.51 | 0.002 | 0.51 | 0.002 |
| PEG 400 | 4.6 | 0.012 | 4.6 | 0.012 |
| Dipropylene Glycol Monoethyl ether | 2 | 0.013 | 2 | 0.013 |
| Water | 62.26 | 3.459 | 62.26 | 3.459 |
| Buffer System | | | | |
| 1  Borax | 10.89 | 0.037 | 10.89 | 0.037 |
| Boric Acid | 10.74 | 0.174 | 10.74 | 0.174 |
| 2  Sodium Carbonate | | | | |
| Sodium Bicarbonate | | | | |
| 3  Potassium Carbonate | | | | |
| Potassium Bicarbonate | | | | |
| 4  Ammonium Chloride | | | | |
| Sodium Hydroxide | | | | |
| 5  Ammonium Citrate Tribasic | | | | |
| 6  Monopotassium phosphate | | | | |
| Dipotassium phosphate | | | | |
| pH of treating solution | 7.5 | | 7.5 | |
| Penetration Zone (average of 10 samples) | 3.0 | | 2.7 | |
| Analytical Proof of Penetration (NAA via I-) | Yes | | Yes | |
| Total | 100 | | 100 | |
| Total Non-Water Components | 37.74 | | 37.74 | |

TABLE 9 shows the use of the amine oxide and ethoxylated castor oil in combination with the fungicide IPBC and borax/boric acid on radiata pine with a successful penetration of 3.0 and yellow poplar with a successful penetration of 2.7.

TABLE 10

| | W | |
|---|---|---|
| | % (m/m) | mol |
| Decyl Dimethyl Amine Oxide (C10) | 5 | 0.015 |
| "Propoxylated" Castor Oil (3100 amu, 56% PO) | 4 | 0.001 |
| IPBC | 0.51 | 0.002 |
| PEG 400 | 4.6 | 0.012 |
| Dipropylene Glycol Monoethyl ether | 2 | 0.013 |
| Water | 62.26 | 3.459 |
| Buffer System | | |
| 1    Borax | 10.89 | 0.037 |
|       Boric Acid | 10.74 | 0.174 |
| 2    Sodium Carbonate | | |
|       Sodium Bicarbonate | | |
| 3    Potassium Carbonate | | |
|       Potassium Bicarbonate | | |
| 4    Ammonium Chloride | | |
|       Sodium Hydroxide | | |
| 5    Ammonium Citrate Tribasic | | |
| 6    Monopotassium phosphate | | |
|       Dipotassium phosphate | | |
|       pH of treating solution | 7.5 | |
| Penetration Zone (average of 10 samples) | 2.9 | |
| Analytical Proof of Penetration (NAA via I-) | Yes | |
| Total | 100 | |
| Total Non-Water Components | 37.74 | |

Referring to Table 10, the amine oxide was present in the amount of 5% (m/m) and the proproxylated castor oil was present in the amount of 4% (m/m). Propoxylated castor oil is an alkoxylated oil which can be made by reacting castor oil with propylene oxide, as contrasted with reacting castor oil with ethylene oxide which would produce ethoxylated castor oil. The amine oxide was decyl dimethyl amine oxide (C10) and the castor oil was 3100 amu, and 56% PO). The remaining constituents were present as in an exact amounts as in TABLE 9. The treating solution has at a pH of 7.9 as compared with 7.5 in TABLE 9 and had a successful penetration of 2.9.

The alkoxylated oil may be present on a total solution weight basis in an amount of 0.5 to 20% and preferably about 1 to 4.

The amine oxide may be present in a total solution weight basis in an amount of about 0.5 to 10% and, preferably, about 0.6 to 5%.

The buffering agent may be present in a total solution weight basis an amount of about 1 to 20% and, preferably, about 2 to 12%. The pH will preferably be about 4.5 to 10.5 and, most preferably, be about 7.5 to 9.5.

The ethoxylated castor oil will preferably have a mixture of carbon lengths in the range of about 6 to 22 and, preferably, about 12 to 16.

Penetration into wood is achieved using a solution which contains a wood preservative, an amine oxide, an alkoxylated oil, and a buffering agent. The wood utilized in the tests was artificially stiffened wood from the spruce, pine and fir category with radiata pine and yellow poplar being used in the test reported in TABLE 9. It has been demonstrated that when an alkoxylated oil, buffer, and amine oxide are incorporated into a wood preservative solution containing one or more of any group of pesticides or insecticides, it exhibits enhanced penetration throughout the wood.

In a preferred embodiment, ethoxylated castor oil at a mass percentage of 4% (m/m) has provided the best penetration improvement. The active amine oxides mass percent in these preferred forms are 3% (m/m). The buffer content is 0.211 moles of borates buffer (from a combination of borax and boric acid).

While the solution could be applied to the wood to be treated in any desired manner, spraying or dipping would generally be the most preferred.

In a preferred practice of the invention, after the solution has been applied to the wood, activation may be achieved to enhance penetration by stacking the wood and wrapping the same in an air-impervious material such as a suitable resinous plastic sheet and allowing the wood to stand at ambient temperature for about eight hours to three days during which additional penetration may be achieved.

While the use of pressure to enhance efficiency of introduction of the wood preservative into the wood is not required, if desired, introduction under the influence of pressure may be employed in combination with the present invention.

While the solutions disclosed and tested are disclosed as the final solution which would be employed, if desired, the solution may be provided in concentrate from with an appropriate amount of the solvent being added to establish the treating solution prior to wood treatment.

While the invention's prime benefit is efficiency of transport of a wood preservative into the wood including difficult to treat woods, such as artificially stiffened wood which have been hardened through kiln processing, for example, the solution and method of the present invention are designed to function to transport wood preservatives into a wide variety of woods to a greater depth than would exist without the combination of the present invention. While the invention is not so limited, examples of commonly used fungicides are IPBC, propiconazole, didecyl dimethyl ammonium chloride (DDAC) and tebuconazole, and examples of commonly used insecticides are permethrin and imidacloprid.

Whereas particular embodiments of the invention have been described herein for purposes of illustration, it will be evident to those skilled in the art that numerous variations of the details may be without departing from the invention as set forth in the appended claims.

What is claimed is:

1. A wood preservative solution comprising
    an amine oxide,
    a wood preservative,
    an alkoxylated oil,
    a buffering agent, and
    a solvent, whereby the interaction of the amine oxide, the alkoxylated oil and the buffering agent in combination will effect a greater depth of penetration than the ingredients individually of said wood preservative into said wood.

2. The solution of claim 1 including,
    said alkoxylated oil being present on a total solution weight basis in an amount of about 0.5 to 20 percent.

3. The solution of claim 1 including,
    said amine oxide being present on a total solution weight basis in an amount of about 0.5 to 10 percent.

4. The solution of claim 1 including,
    said buffering agent being present on a total solution weight basis in an amount of about 1 to 20 percent.

5. The solution of claim 2 including,
    said alkoxylated oil being present on a total solution weight basis in an amount of about 1 to 4 percent.

6. The solution of claim 5 including,
    said amine oxide being present on a total solution weight basis in an amount of 0.6 to 5 percent.

7. The solution of claim 6 including,
said buffering agent being present on a total solution weight basis in an amount of about 2 to 12 percent.
8. The solution of claim 1 including,
said solution characterized by having the property of creating enhanced wood preservative penetration in artificially stiffened wood.
9. The solution of claim 4 including,
said buffering agent selected from the group consisting of Borax/Boric Acid, Sodium Carbonate/Sodium Bicarbonate, Potassium Carbonate/Potassium Bicarbonate, Ammonium Chloride/Sodium Hydroxide, Ammonium/Citrate Tribasic and Monopotassium phosphate/Dipotassium phosphate.
10. The solution of claim 9 including,
said buffering agent being Borax/Boric Acid.
11. The solution of claim 1 including,
said solution employing water as a solvent.
12. The solution of claim 2 including,
said alkoxylated oil being selected from the group consisting of ethoxylated castor oils and propoxylated castor oil.
13. The solution of claim 2 including,
said ethoxylated castor oil being selected from the group consisting of ethoxylated tall oil, ethoxylated soya oil and groundnut oil.
14. The solution of claim 2 including,
said solution having a pH of about 4.5 to 10.5.
15. The solution of claim 2 including,
said solution having pH of about 7.5 to 9.5.
16. The solution of claim 3 including,
said amine oxide having a carbon length distribution of about 6 to 22.
17. The solution of claim 16 including,
said amine oxide having a carbon length distribution of about 12 to 16.
18. A method of preserving wood including,
providing a wood preservative solution having an amine oxide,
a wood preservative,
an alkoxylated oil,
a buffering agent,
a solvent, and
employing said solution to treat wood by introducing said solution into said wood, whereby the interaction of the amine oxide, the alkoxylated oil and the buffering agent in combination will effect a greater depth of penetration than the ingredients individually of said wood preservative into said wood.
19. The method of claim 18 including,
said alkoxylated oil being present on a total solution weight basis in an amount of 0.5 to 20 percent.
20. The method of claim 18 including,
said amine oxide being present on a total solution weight basis in an amount of about 0.5 to 10 percent.
21. The method of claim 18 including,
said buffering agent being present on a total solution weight basis in an amount of about 1 to 20 percent.
22. The method of claim 18 including,
said solution characterized by having the property of effecting enhanced penetration in artificial stiffened wood.
23. The method of claim 18 including,
said solution employing water as a solvent.
24. The method of claim 19 including,
said alkoxylated oil being present on a total solution weight basis in an amount of about 1 to 4 percent.
25. The method of claim 19 including,
said alkoxylated oil being selected from the group consisting of ethoxylated castor oil and propoxylated castor oil.
26. The method of claim 19 including,
said alkoxylated oil being selected from the group consisting of ethoxylated tall oil, ethoxylated soya oil and ethoxylated groundnut oil.
27. The method of claim 19 including,
said solution having a pH of about 4.5 to 10.5.
28. The method of claim 20 including,
said amine oxide having a carbon length distribution of about 6 to 22.
29. The method of claim 22 including,
said buffering agent selected from the group consisting of Borax/Boric Acid, Sodium Carbonate/Sodium Bicarbonate, Potassium Carbonate/Potassium Bicarbonate, Ammonium Chloride/Sodium Hydroxide, Ammonium Citrate Tribasic and Monopotassium phosphate/Dipotassium phosphate.
30. The method of claim 20 including,
said amine oxide being present on a total solution weight basis in an amount of about 0.6 to 5 percent.
31. The method of claim 21 including,
said buffering agent being present on a total solution weight basis in an amount of about 2 to 12 percent.
32. The method of claim 28 including,
said amine oxide having a carbon length distribution of about 12 to 16.
33. The method of claim 27 including,
said solution having a pH of about 7.5 to 9.5.
34. The method of claim 29 including,
said buffering agent being Borax/Boric Acid.
35. The method of claim 27 including,
activating said treated wood.
36. A wood preservative solution comprising,
an amine oxide,
a wood preservative,
an alkoxylated oil,
a buffering agent, and
a solvent, whereby the interaction of the amine oxide, the alkoxylated oil, the buffering agent in combination will effect a greater depth of penetration than the ingredients individually of said wood preservatives into artificially stiffened wood.
37. The solution of claim 36 including,
said alkoxylated oil being present on a total solution weight basis in an amount of about 1 to 4 percent.
38. A method of preserving wood including,
providing a wood preservative solution having an amine oxide,
a wood preservative,
an alkoxylated oil,
a buffering agent,
a solvent, and
employing said solution to treat wood by introducing said solution into said wood, whereby the interaction of the amine oxide, the alkoxylated oil,
the buffering agent in combination will effect a greater depth of penetration than the ingredients individually of said wood preservatives into artificially stiffened wood.
39. The method of claim 38 including,
said alkoxylated oil being present on a total solution weight basis in an amount of about 1 to 4 percent.

* * * * *